United States Patent [19]

Brennan

[11] Patent Number: 5,091,525
[45] Date of Patent: Feb. 25, 1992

[54] MONOHYDRATE AND DMF SOLVATES OF A NEW CARBACEPHEM ANTIBIOTIC

[75] Inventor: John Brennan, Indianapolis, Ind.

[73] Assignee: Eli Lilly and Company, Indianapolis, Ind.

[21] Appl. No.: 601,021

[22] Filed: Oct. 23, 1990

Related U.S. Application Data

[63] Continuation of Ser. No. 488,414, Mar. 1, 1990, abandoned, which is a continuation of Ser. No. 379,723, Jul. 14, 1989, abandoned, which is a continuation of Ser. No. 105,762, Oct. 7, 1987, abandoned.

[51] Int. Cl.$^5$ ............................................. C07D 463/00
[52] U.S. Cl. ................................................... 540/205
[58] Field of Search .......................................... 540/205

[56] References Cited

U.S. PATENT DOCUMENTS

| | | | |
|---|---|---|---|
| 3,506,645 | 4/1970 | Flitter | 540/320 |
| 3,655,656 | 4/1972 | Von Heyningen | 540/230 |
| 3,697,506 | 10/1972 | Butler | 540/342 |
| 3,957,773 | 5/1976 | Burton et al. | 260/243C |
| 4,160,863 | 7/1979 | Bouzard | 540/230 |
| 4,260,543 | 4/1981 | Miller | 540/350 |
| 4,335,211 | 6/1982 | Hashimoto | 435/50 |
| 4,882,325 | 11/1989 | Godtfredsen | 540/320 |

OTHER PUBLICATIONS

Merck Index, 10th Edition (1983), pp. 267–8.
Merck-Index, 10th Edition, Entry 1896.
Herman, Chem. Abs. 94, 90151t (1980).

*Primary Examiner*—Mark L. Berch
*Attorney, Agent, or Firm*—James J. Sales; Leroy Whitaker

[57] ABSTRACT

The crystalline monohydrate, mono (N,N'-dimethylformamide) and bis(N,N'-dimethylformamide) solvates of 7β-[2'-(R)-2'-(p-hydroxyphenyl-2'-amino-acetamido]-3-chloro-3-(1-carbadethiacephem)-4-carboxylic acid ("LY213735") are novel compounds with superior physical characteristics. Also described are pharmaceutical formulations of crystalline LY213735 monohydrate.

4 Claims, No Drawings

MONOHYDRATE AND DMF SOLVATES OF A NEW CARBACEPHEM ANTIBIOTIC

This application is a continuation of application Ser. No. 07/488,414, filed on Mar. 1, 1990, which is a continuation of application Ser. No. 07/379,723, filed on July 14, 1989, which is a continuation of application Ser. No. 07/105,762, filed on Oct. 7, 1987, all now abandoned.

INTRODUCTION

The β-lactam antibiotic of the formula

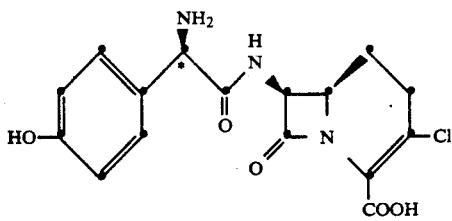

is a potent new orally-active antibiotic. The antibiotic is described, for example, in J. Hashimoto et al., U.S. Pat. No. 4,335,211, issued June 15, 1982. For brevity's sake, the compound will be referred by the serial number LY213735. Thus, the instant invention is directed to the monohydrate and the mono- and bis-(N,N'-dimethylformamide) solvates of LY213735. (The latter two solvates will be referred to hereinafter as the "mono(DMF)" and "bis(DMF)" solvates, respectively).

LY213735 monohydrate ("monohydrate") is a pharmaceutically elegant hydrate of LY213735. The monohydrate affords a necessary form of LY213735 useful in the manufacture of the various dosage forms of the antibiotic. The mono(DMF) and bis(DMF) solvates are convenient intermediates to LY213735 in general and the monohydrate specifically.

SUMMARY OF THE INVENTION

One aspect of the present invention is directed to the crystalline monohydrate of LY213735. The formula for LY213735 is given below as Formula I. More specifically, the invention is directed to LY213735 monohydrate having the x-ray powder diffracion pattern listed below in Table 1. A related aspect are pharmaceutical formulations of LY213735 monohydrate, of which pharmaceutical formulations containing crystalline LY213735 monohydrate having the x-ray pattern listed in Table 1.

Another aspect of the invention is the mono(DMF) solvate of LY213735. A preferred form of the mono(DMF) solvate is a crystalline compound having the x-ray powder diffraction pattern listed below in Table 2.

Yet another aspect of the instant invention is the bis(DMF) solvate of LY213735. A preferred form of the bis(DMF) solvate is a crystalline compound having the x-ray powder diffraction pattern listed below in Table 3.

The mono- and bis(DMF) solvates are convenient intermediates to the corresponding monohydrate of LY213735. The monohydrate affords a stable, easy-to-handle form of LY213735, a compound that here-to-fore was both difficult to purify and obtain in a pharmaceutically elegant form.

DETAILED DESCRIPTION

The instant invention is directed to the crystalline monohydrate and to the crystalline mono- and bis(DMF) solvates of the compound of Formula I:

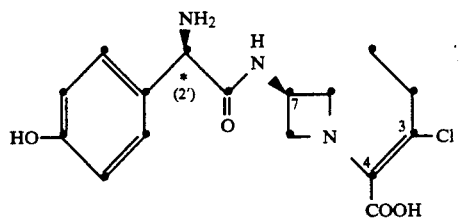

In the present solvates and hydrate of Formula I the C-2' asymmetric center has the R absolute configuration. Furthermore, the instant solvates and monohydrate (and pharmaceutical compositions of the monohydrate) may encompass the zwitterionic form of the compound of 20 Formula I. For brevity's sake, the compound of Formula I will be referred to as "LY213735", and the compounds of the instant invention as "LY213735 monohydrate", "monohydrate" or "crystalline monohydrate", or "LY213735 mono(DMF) solvate", "mono(DMF) solvate", "LY213735 bis(DMF) solvate", or "bis(DMF) solvate", and the like. It will be understood that these abbreviated terms refer to the crystalline or microcrystalline form of the monohydrate or the two solvates.

Finally, the instant invention also encompasses pharmaceutical compositions of the crystalline LY213735 monohydrate, and preferably of the monohydrate exhibiting the crystal pattern listed below in Table 1.

A preferred embodiment of the invention is a crystalline monohydrate exhibiting the x-ray powder diffraction pattern of Table 1:

TABLE 1

| Monohydrate | |
|---|---|
| d | $I/I_1$ |
| 12.99 | .17 |
| 10.76 | 1.00 |
| 9.11 | .33 |
| 7.43 | .14 |
| 6.65 | .12 |
| 5.75 | .05 |
| 5.24 | .04 |
| 5.06 | .16 |
| 4.87 | .24 |
| 4.74 | .23 |
| 4.41 | .23 |
| 4.30 | .18 |
| 4.13 | .12 |
| 3.90 | .27 |
| 3.59 | .22 |
| 3.37 | .53 |
| 3.20 | .12 |
| 2.94 | .10 |
| 2.86 | .06 |
| 2.73 | .06 |

The diffraction pattern in Table 1 was obtained with nickel-filtered radiation of wavelength $\lambda = 1.5406$ Å. The interplanar spacings are in the column marked "d" and the relative intensities are in the column marked "$I/I_1$".

Another preferred embodiment of the instant invention is the crystalline mono(DMF) solvate exhibiting the x-ray powder diffraction pattern set forth below in Table 2:

TABLE 2

| Mono(DMF) Solvate | |
|---|---|
| d | $I/I_1$ |
| 13.18 | .12 |
| 10.90 | 1.00 |
| 7.69 | .11 |
| 6.80 | .07 |
| 6.02 | .20 |
| 5.37 | .07 |
| 5.12 | .10 |
| 4.90 | .07 |
| 4.69 | .27 |
| 4.37 | .43 |
| 3.93 | .25 |
| 3.57 | .15 |
| 3.40 | .23 |
| 3.22 | .10 |
| 3.08 | .05 |
| 2.85 | .0 |
| 2.74 | .15 |

(The x-ray data in Table 2 was collected with the same instrument parameters used to collect the data in Table 1.)

Still another preferred embodiment of the invention is a crystalline form of the bis(DMF) solvate exhibiting the x-ray powder diffraction data listed in the following Table 3:

TABLE 3

| Bis(DMF) Solvate | |
|---|---|
| d | $I/I_1$ |
| 20.1 | .03 |
| 12.44 | 1.00 |
| 10.27 | .07 |
| 8.58 | .08 |
| 6.91 | .03 |
| 6.60 | .05 |
| 6.23 | .08 |
| 5.43 | .13 |
| 4.74 | .09 |
| 4.41 | .09 |
| 4.19 | .40 |
| 3.62 | .05 |
| 3.52 | .05 |
| 3.39 | .03 |
| 3.34 | .03 |
| 3.14 | .10 |
| 3.02 | .07 |
| 2.86 | .06 |

(The x-ray data in Table 3 was collected with the same instrument parameters as those used to collect the data in Table 1.)

A further aspect of this invention is the pharmaceutical compositions of crystalline LY213735 monohydrate. In particular, these pharmaceutical compositions are useful for the control of gram-positive and gram-negative bacterial infections in warm-blooded animals and comprise a suitable vehicle and a therapeutically effective amount of the LY213735 monohydrate.

With regard to compositions for oral administration (such as tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose, and starch; fillers and carriers, for example corn starch, gelatin, lactose, sucrose, microcrystalline cellulose, kaolin, mannitol, dicalcium phosphate, sodium chloride, and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions of the present invention may also be in the form of oral liquid preparations, which may be either a) aqueous or oily suspensions, solutions, emulsions or syrups; or b) a dry powder to be reconstituted with water or another suitable vehicle before use. When used in conjunction with such oral liquid preparations, the term "suitable vehicle" means conventional additives such as suspending agents such as acacia, methyl cellulose, hydroxyethyl cellulose, carboxymethyl cellulose, cellulose with sodium carboxymethyl cellulose (Avicel®), xantham gum, or starch; sweeteners such as sucrose, syrup, glucose, saccharin, sorbital, or aspartame; wetting agents such as sodium lauryl sulfate, silicone oil, the various Pluromics® surfactants, or glycerin; preservatives such as methyl, propyl, or butyl p-hydroxy benzoates, or sorbic acid; dyes, flavors and salts such as sodium chloride, citric acid, oil of wintergreen or sodium citrate; and waters, oils, and esters such as almond oil, fractionated coconut oil, hydrogenated caster oil, lecithin, aluminum stearate, and the like.

The pharmaceutical composition can also be for intravenous (IV) use. Specifically, a water soluble form of the monohydrate compound can be dissolved in one of the commonly used intravenous fluids and administered by infusion. When used in conjunction with compositions for IV use, the term "suitable vehicle" means such fluids as physiological saline, Ringer's solution or 5% dextrose solution.

Topical compositions can be formulated with "suitable vehicles" such as hydrophobic or hydrophilic bases. Such bases include ointments, creams or lotions.

Veterinary pharmaceutical compositions of the crystalline monohydrate compound may be administered in the feed or the drinking water of farm animals. Alternatively, the compounds can be formulated as intramammary preparations with "suitable vehicles" such as long- or quick-release bases.

The crystalline monohydrate compound of Formula I can also be formulated in unit dosage form in sterile vials, sterile plastic pouches containing a port with a septum, or sterile, hermetically sealed ampoules. The amount of the monohydrate compound per unit dosage may vary from about 100 milligrams to about 10 grams.

A "therapeutically effective amount" of the crystalline monohydrate is from approximately 2.5 mg to about 70 mg of compound per kilogram of body weight per dose. This amount generally totals from about 1 gram to about 5 grams per day for an adult human.

The dose can be administered in a single daily dose or in multiple doses per day. The treatment regimen with the instant formulations may require administration over extended periods of time, for example, for several days or for from two to three weeks. The amount administered per dose or the total amount administered will depend on such factors as the nature and severity of the infection, the age and general health of the patient, and the tolerance to the monohydrate compound of both the patient and the microorganism or microorganisms involved in the infection.

A preferred group of pharmaceutical formulations are formulations comprising a suitable vehicle of the crystalline monohydrate exhibiting the x-ray pattern of Table 1, above.

The monohydrate can be made from either the mono(DMF) or bis(DMF) solvate. For instance, the bis(DMF) solvate, along with tetrasodium EDTA and a small amount of concentrated hydrochloric acid, are combined in water. After the suspension went to a solution, the solution was cooled (to approximately 10° C.) and the pH was raised slowly (by the addition of a base such as triethylamine) until a suspension formed (for example, pH 3.6). The suspended solid (which is the monohydrate) is collected by filtration, washed and dried in the usual manner. Alternatively, the mono(DMF) compound can be converted to the monohydrate under conditions similar to those for the conversion of the bis(DMF) solvate. Upon addition of the base, the pH of the mono(DMF) solution occasionally goes to a higher pH than the pH of the bis(DMF) (for example, a pH of 5.8) for a similar amount of base.

The bis(DMF) solvate may result from the acylation of a 7β-amino ("nucleus") compound of the Formual II

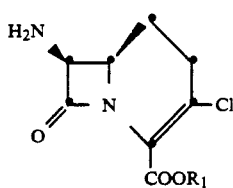
II then removing the carboxy-protecting group represented above as $R_1$.

The carboxy-protecting group $R_1$ of Formula II is a conventional carboxy-protecting group and preferably one which is not sterically hindered. Examples of such groups are the benzyl group and substituted benzyl groups such as 4-methoxybenzyl, 4-nitrobenzyl, 4-methylbenzyl, 3,5-dimethylbenzyl, and 4-chlorobenzyl; silyl groups such as a trialkylsilyl group (in particular, trimethylsilyl); and halo-substituted alkyl groups such as the 2,2,2-trichloroethyl, 2,2,2-tribromoethyl, and 2-iodoethyl groups. A preferred ester group is the benzyl or a substituted benzyl ester group (such as the p-nitrobenzyl group).

In particular, the acylation of the p-nitrobenzyl nucleus compound ($R_1$=para-nitrobenzyl takes place in cooled (for example, −20° C.) DMF. The acylating agent, an activated derivative of 2-(R)-2-(p-hydroxyphenyl)-2-aminoacetic acid, is added to the cooled DMF. A preferred acylating agent is a compound of the formula III

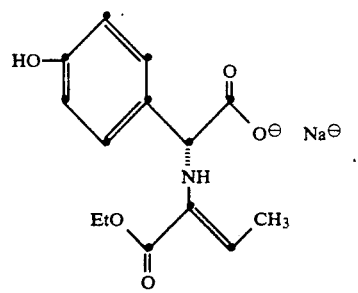
III

The reaction solution is cooled, and when III is the acylating agent, methanesulfonic acid, dimethylbenzylamine, and methyl chloroformate are added in rapid succession. The solution is stirred and maintained at a very low (approximately −50° C.) temperature, then the pNB ester of the nucleus is added with stirring. The reaction is stirred at low temperature (for example, −45° C.) until the acylation reaction is substantially complete (as determined by conventional means such as thin layer chromatography). The mixture is then warmed slowly approximately −10° C. and the reagents for removing the amino and carboxy protecting groups (such as water, concentrated hydrochloric acid, and zinc dust for the pNB ester) are added slowly while maintaining the initial temperature of the solution. The solution is stirred at room temperature until the reaction is complete. In the case where $R_1$ was the pNB ester the pH is raised (for example to 2.9) by the addition of a base such as triethylamine, and the resultant zinc residue is removed by filtration. The pH is gradually taken higher until a white suspension formed and the pH remained stable without the addition of base (typically around pH 5.6). (The mixture was seeded with LY213735 at about pH 4.6 to induce crystall-ization). The solid phase of the suspension is collected by filtration. The wet filter cake is suspended in a 90:10 mixture of 9:1 DMF/H$_2$O and solution effected with concentrated hydrochloric acid. The solution is cooled and the pH raised in small increments with a base (triethylamine) until a suspension formed and the pH of the solution stabilized with further additions of base (for example, a pH of approximately 5.7). The crystals again collected by filtration and dried to give the bis(DMF) solvate.

Alternatively, the bis(DMF) solvate can be made from a concentrated DMF solution of mono(DMF) solvate. Specifically, anti-solvent (preferably acetonitrile) is added in equal volume to the concentrated DMF solution and the mixture is cooled (for example, to 0° C.). The solid bis(DMF) precipitate is collected by filtration as above.

The mono(DMF) solvate often results from the acylation reaction used for making the bis(DMF) solvate. Another way of making the mono(DMF) solvate entails suspending the bis(DMF) solvate in a minimum amount of cool 9:1 DMF:H$_2$O then effecting solution with the minimum amount of acid (such as concentrated hydrochloric acid). The pH of the solution is slowly raised with base (such as triethylamine) until a light suspension forms (typically around pH 3.0). The suspension is filtered (which removes triethylammonium chloride) then the pH of the filtrate is slowly raised to 5.8 by the addition of base. The monohydrate crystals are collected by filtration and dried.

Many alternate methods exist for the acylation of the nucleus compound (Formula II) to give LY213735. LY213735 obtained from these alternate methods could be converted to either one of the two instant DMF solvates by suspending the acylated product compound in a water/DMF mixture, then effecting solution with acid and inducing precipitation with base, as described above. The acylation methods for LY213735 are similar to the methods for the acylation of 6-aminopenicillanic acid, 7-aminodesacetoxycephalosporanic acid, and 7-aminocephalosporanic acid. One acylation method is to simply combine the 7β-amino nucleus with an acid chloride or acid bromide in the presence of an acid scavenger. The acid chloride or acid bromide may be formed in situ. Another method is to combine the 7β-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di(n-propyl)carbodiimide, N,N'-di(iso-propyl)-carbodiimide, N,N'-diallylcarbodiimide, N,N'-bis(p-dimethylaminophenyl)carbodiimide, N-ethyl-N'-(4''-ethylmorpholinyl)carbodiimide, and the like. Other suitable carbodiimide condensing agents are disclosed by Sheehan in U.S. Pat. No. 2,938,892, and by Hofmann et al. in U.S. Pat. No. 3,065,224. Azolides, such as N,N'-carbonyldiimidazole and N,N'-thionyldiimidazol, may also be used as condensing agents. Dehydrating agents such as phosphorus oxychloride, the alkoxyacetylenes, and 2-halogenopyridinium salts (such as 2-chloropyridinium methyl iodide, 2-fluoropyridinium methyl iodide, and the like) may be used to couple the free acid or its acid salt with the 7β-amino nucleus.

Another acylation method entails first converting the free carboxylic acid form (or the corresponding salt) of the acyl side chain to the corresponding active ester derivative, which is in turn used to acylate the nucleus. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy-6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl, and iso-but-2-ylcarbonyl, and the carboxylic acid of the acyl side chain. The mixed anhydrides are synthesized by acylating the carboxylic acid of the acyl side chain.

Alternatively, the 7β-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (such as tetrahydrofuran, acetonitrile, and the like). The resultant EEDQ derivative is used in situ to acylate the 7β-amino nucleus.

Yet another method of acylating the 7β-amino compounds entails the use of an enzymatically-assisted process. Such a process is described in Hashimoto et al., U.S. Pat. No. 4,335,211, issued June 15, 1982, herein incorporated by reference.

The amino- and carboxy-protecting groups are removed by methods well known in the art. Examples of conditions for the removal of these two types of protecting groups can be found in standard works on the subject such as E. Haslam, "Protective Groups in Organic Chemistry", J. G. W. McOmie, Ed., Plenum Press, New York, N.Y., 1973, Chapters 2 and 5, and T. W. Greene, "Protective Groups in Organic Synthesis", John Wiley and Sons, New York, N.Y., 1981, Chapters 5 and 7, respectively.

Examples of procedures for the removal of amino- and carboxy-protecting groups can also be found in the Experimental Section. For example, the t-butoxycarbonyl amino-protecting group was removed with trifluoroacetic acid, and the p-nitrobenzyl carboxy-protecting group was removed by hydrogenolysis.

The 7β-amino 3-chloro 1-carba-1-dethiacephem compound of Formula II are synthesized from the corresponding 3-hydroxy compounds in accord with the process diagrammed below in Scheme 1:

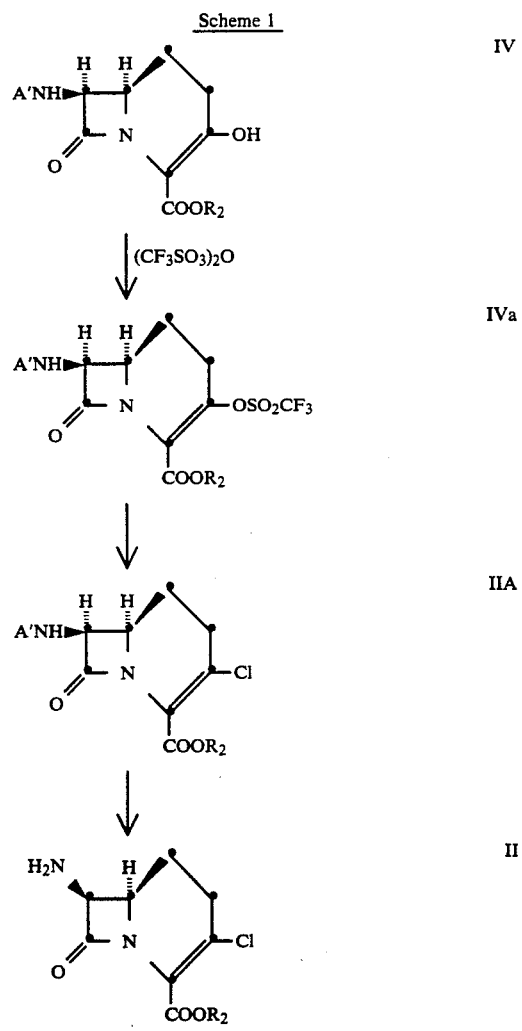

In the above Scheme 1, $R_2$ is a carboxy-protecting (as described above for Formula II) and A is either an amino-protecting group or an acyl group of the formula

R—CO— wherein R is:

hydrogen, $C_1$ to $C_6$ alkyl, $C_1$ to $C_6$ alkyl substituted by cyano, carboxy, halogen, amino, $C_1$ to $C_4$ alkoxy, $C_1$ to $C_4$ alkylthio, or trifluoromethylthio; a phenyl or substituted phenyl group represented by the formula

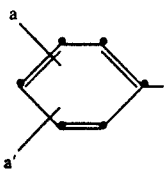

wherein a and a' independently are hydrogen, halogen, protected hydroxy, $C_1$ to $C_4$ alkoxy, $C_1$ to $C_4$ alkanoyloxy, $C_1$ to $C_4$ alkyl, $C_1$ to $C_4$ alkylthio, protected amino, $C_1$ to $C_4$ alkanoylamino, $C_1$ to $C_4$ alkylsulfonylamino, protected carboxy, carbamoyl, protected hydroxymethyl, protected aminomethyl, or protected carboxymethyl;
a group represented by the formula

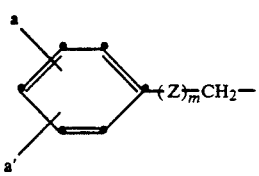

wherein a and a' have the same meanings as defined above, Z is O or S, and m is 0 or 1; a heteroarylmethyl group represented by the formula

$R_3$—$CH_2$— wherein $R_3$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by protected amino, protected hydroxy, halogen, $C_1$ to $C_4$ alkyl, $C_1$ to $C_4$ alkoxy, or $C_1$ to $C_4$ alkylsulfonylamino groups;
a substituted methyl group represented by the formula

$R_4$—CH—
       |
       Q wherein $R_4$ is cyclohex-1,4-dienyl, a phenyl group or a substituted phenyl group represented by the formula

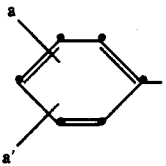

wherein a and a' have the above defined meanings, or $R_4$ is $R_3$ as defined above, and Q is protected hydroxy, $C_1$ to $C_4$ alkanoyloxy, protected carboxy, sulfo, or protected amino.

The sulfonylation of the 3-hydroxy group represented by the first reaction in above Scheme I (Formula IV→Formula IVa) is carried out in an inert solvent at a temperature between about 0° C. and about 35° C. in the presence of a tertiary amine. Amines which are suitable include triethylamine, tri-(n-butyl)amine, pyridine, t-butyldiethylamine, di(isopropyl)ethylamine, and like amines. Hindered trialkylamines are preferred. The acylating reagent can be trifluoromethanesulfonic anhydride (triflic anhydride), trifluoromethanesulfonyl chloride (triflic chloride) or other suitable acid derivatives of trifluoromethanesulfonic acid. Inert solvents useful in the process are the halogenated hydrocarbons such as chloroform, methylene chloride, trichloroethane, and the like; ether solvents such as tetrahydrofuran; esters such as ethyl acetate; or other inert solvents such as acetonitrile.

The triflic esters (Formula IVa) are recovered from the reaction mixture by conventional isolation methods, such as by extraction.

During the acylation any reactive groups in the side chain group $R_1$ also capable of acylation is desirably protected. For example, any amino group substituents are protected with a conventional amino-protecting group to prevent amide formation in competition with the desired sulfonylation formation.

The second (chlorination) reaction in the above Scheme 1 (Formula IVa→Formula IIa) proceeds with lithium chloride in an aprotic solvent at a temperature between about 60° C. and about 95° C.

Aprotic polar solvents which can be used in the chlorination reaction are dimethylformamide, dimethylacetamide, N-methylpyrrolidone, acetonitrile, and like solvents. Dimethylformamide is a preferred solvent.

Preferably the reaction is carried out at a temperature between about 75° C. and about 85° C. with an excess of the stoichiometric amount of the lithium chloride salt.

A preferred carboxy-protecting group at $R_2$ is the benzyl or a substituted benzyl group.

Following completion of the chlorination reaction the 3-chloro-1-carba-3-cephem ester is recovered from the reaction mixture by conventional isolation methods and is purified by chromatography.

As with the first reaction in Scheme 1, during the chlorination reaction it is desirable to protect any amino groups present in the starting material. In an example of the reaction, benzyl 7β-phenoxyacetylamino-3-trifluoromethylsulfonyloxy-1-carba-1-dethiacephem-4-carboxylate is dissolved in dimethylformamide and an excess (such as a 3 to 4 molar excess) of lithium chloride is added. The solution is stirred and heated to a temperature of about 80° C. for about 5 to 6 hours. The progress of the chlorination can be followed by thin layer chromatography of a small aliquot periodically removed from the reaction mixture. When the reaction is completed the mixture is diluted with a water-immiscible organic solvent, washed with water, dried, and evaporated. The crude product (benzyl 7β-phenoxyacetylamino-3-chloro-1-carba-1-dethiacephem-4-carboxylate) is purified by chromatography (for example, over silica gel).

The conversion of the 3-hydroxy compound (Formula IV) to the 3-chloro compound (Formula IIA) as depicted above in Scheme 1 is also described in David A. Evans et al., U.S. Pat. No. 4,673,727, issued June 16, 1987, Levin incorporated by reference.

The final reaction in the above Scheme 1, which is either the removal of the amino-protecting group or the cleavage of the amido group represented by the partial formula "A'NH—" (Compound IIa→Compound II) are reactions well known in the art. The removal of amino-protecting groups are taught in the references mentioned above for the acylation and subsequent deprotection of the compounds of Formula II.

The methods for cleaving the amide bond of a 7-(amido) side chain are well known in the art. One such method employs nitrosyl chloride, as exemplified in M. Stamper et al., U.S. Pat. No. 3,507,862, issued Apr. 21, 1970, herein incorporated by reference. Another method uses phosphorus pentachloride in the presence of a (preferably nitrogen) base. The latter process is described in, for example, R. Chauvette, U.S. Pat. No. 3,549,628, issued Dec. 22, 1970, B. Fechtig et al., U.S. Pat. No. 3,697,515, issued Oct. 10, 1972, and L. Hatfield, U.S. Pat. No. 3,868,368, issued Feb. 25, 1975, all three of which are herein incorporated by reference.

An improved version of the above phosphorous pentachloride method employs a triphenylphosphite-chlorine kinetic reagent, as discussed in L. Hatfield et al., U.S. Pat. No. 4,211,702, issued July 8, 1980, herein incorporated by reference. An excess (2 to 3 equivalents) of this reagent can be used to both cleave the 7-amido group and chlorinate the 3-hydroxy group of the 3-enol 1-carba-1-dethiacephem (for example, the compounds of Formula III above) analogous to the conditions set forth in L. Hatfield et al., U.S. Pat. No. 4,226,986, issued Oct. 7, 1980, herein incorporated by reference.

Yet another method for synthesizing the 7-amino compounds of Formula II is the method set forth in T. Hirata et al., U.K. Patent Application No. 2,041,923A and its equivalents (such as European Patent Application No. 14,475A). This method entails, in general, addition of a phenylthiol to a 7-azido 3-hydro-1-carba-1-dethia-4-carboxylate compound. The resulting 3-thio-3,4-saturated compound is oxidized to the corresponding 3-sulfoxide compound. The 3-sulfoxide compound is chlorinated and the resultant 3-sulfoxide-3-chloro compound is treated with base (to eliminate the sulfoxide) to give the 3-chloro-3-cephem compound.

The 3-hydroxy starting materials (Formula IV) of Scheme 1 are prepared as described in David A. Evans et al., U.S. Pat. No. 4,665,171, issued May 12, 1987, herein incorporated by reference. (For a related discussion, see also David A. Evans et al., *Tetrahdron Letters*, 26, pp. 3783–3786 and 3787–3790 (1985)). As described therein, an asymmetric process for the preparation of 3-hydroxy-1-carbacephalosporins is provided. According to the process, a 3β-[4-(S)-aryloxazolidin-2-one-3-yl-azetidin-2-one is prepared and converted asymmetrically to a 7-amino-protected or 7-acylamino 3-hydroxy-1-carba-1-dethiacephalosporin. The azetidin-2-one is represented by the formula 1:

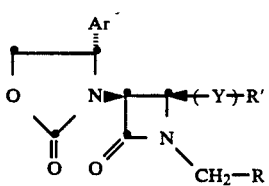

wherein Ar is phenyl, $C_1$-$C_4$ alkylphenyl, halophenyl, $C_1$-$C_4$ alkoxyphenyl, naphthyl, thienyl, furyl, benzothienyl, or benzofuryl; $R_1$ is phenyl, $C_1$ to $C_4$ alkylphenyl, $C_1$-$C_4$ alkoxyphenyl, or halophenyl; Y is a group of the formula —CH=CH— or —CH$_2$—CH$_2$—; and R' is phenyl, $C_1$ to $C_4$ alkylphenyl, $C_1$ to $C_4$ alkoxyphenyl, halophenyl, furyl or naphthyl.

Preferred azetidinones are represented by the formula 1 when Ar and $R_1$ are phenyl or substituted phenyl, and R' is phenyl, substituted phenyl, or furyl.

Examples of such preferred compounds are 1-benzyl-3β-[4-(S)-phenyloxazolidin-2-one-3-yl]-4β-styrylazetidin-2-one, 1-benzyl-3β-[4-(S)-phenyloxazolidin-2-one-3-yl-4β-(3-methoxystyryl)azetidin-2-one, and 1-benzyl-3β-[4-(S)-phenyloxazolidin-2-one-3-yl]-4β-[2-(2-furyl)ethenyl]-azetidin-2-one.

The azetidinones of formula 1 are obtained by the cycloaddition of a 4-(S)-aryloxazolidin-2-one-3-ylacetyl halide and an imine formed with a benzylamine and a 3-arylacrolein. The acid halide is converted in situ with a trialkylamine to the corresponding homochiral ketene. Upon cycloaddition the ketene and imine provide the azetidinone. Alternatively, the ketene can be generated with the anhydride of the oxazolidinone acetic acid and trifluoroacetic acid, or with phosphoryl chloride or phosphoryl bromide. The cycloaddition reaction is a key step in the asymmetric process for the preparation of 1-carba-1-dethiacephalosporins.

The 4-(S)-aryloxazolidin-2-one-3-ylacetyl halide employed in the cyclization is obtained with an L-arylglycine represented by the formula 1a

wherein Ar has the same meanings as defined above. The preparation is illustrated in the following reaction scheme:

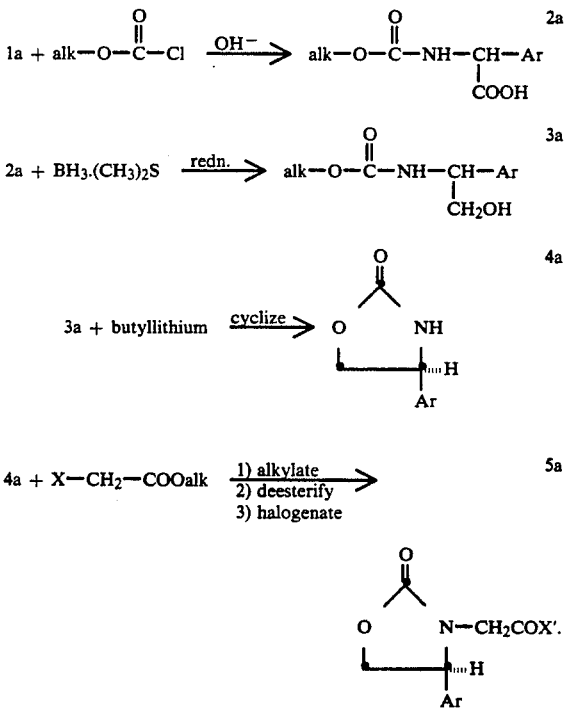

In the above scheme "alk" refers to $C_1$ to $C_4$ alkyl, such as methyl, ethyl, n-propyl, and t-butyl; X refers to halogen, preferably chloro or bromo; X' is chloro, bormo, trifluoroacetoxy, or —OP(=O)X$_2$, wherein X is halogen; and Ar has the same meanings as previously defined.

In carrying out the preparation of the 4-aryloxazolidinone 4a the L-arylglycine is first converted to the carbamate 2a. The arylglycine is dissolved in aqueous base by utilizing only the amount of base needed to form the soluble salt plus a small excess. The solution is cooled to a temperature between about 0° C. and about 10° C. and non-stoichiometric amounts of the haloformate are added in several portions with stirring. Additional base is added to redissolve the arylglycine and additional haloformate is added portionwise with stirring. This process is repeated in the cold until an amount in excess of the stoichiometric amount of haloformate has been added and carbamate formation is completed. The reaction is preferably carried out as rapidly as possible. The hydroxide ion necessary for the reaction is best supplied by the alkali metal hydroxides (for example, sodium hydroxide and potassium hydroxide). Preferably 3N sodium hydroxide.is used. The L-carbamate derivative 2a is recovered from the reaction mixture by acidification and extraction of the precipitated carbamate with a water immiscible solvent (like a halogenated hydrocarbon solvent such as dichloromethane).

The L-carbamate 2a is reduced with excess borane-dimethylsulfide in tetrahydrofuran at a temperature between about 20° C. and about 40° C. to provide the L-alcohol 3a. The borane-dimethylsulfide reagent is added to a solution of the carbamate acid in tetrahydrofuran cooled to about 0° C. and the mixture is stirred at the temperature range, conveniently at room temperature, for about 10 hours to 20 hours. The excess borane is destroyed by quenching the mixture with water and the alcohol 3a is recovered by concentrating the mixture by evaporation, diluting the concentrate with more water if necessary, and extracting the alcohol with a water immiscible solvent such as methylene chloride. The recovered alcohol is of sufficient purity to use directly in the cyclization to compound 4a, however, it may be further purified prior to use by recrystallization.

The L-alcohol 3a is then cyclized to the (S)-4-aryloxazolidin-2-one (4a) with n-butyllithium or an alkali metal alkoxide such as lithium or sodium ethoxide in an inert solvent. n-Butyllithium is the preferred base and is generally used in an amount less than the stoichiometric amount. The reaction is carried out for from 2 to 8 hours at a temperature between about 25° C. and about 65° C. and preferably at about 55° C. Suitable inert solvents are tetrahydrofuran, 1,2-dimethoxyethane, and like ethers. After completion of the cyclization, the reaction mixture is treated with acetic acid in an amount corresponding to the amount of base used. The acidified mixture is concentrated and the oxazolidin-2-one (4a) is recovered from the concentrate by extraction with a suitable organic solvent such as methylene chloride, chloroform, or trichloroethane.

The (S)-4-aryloxazolidin-2-one (4a) is N-alkylated with a haloacetic acid ester, the ester deesterified, and the acid converted to the acyl halide (5a).

The alkylation of the oxazolidinone 4a with the haloacetic acid ester is carried out with sodium hydride in dimethylformamide or tetrahydrofuran to provide the (S)-4-aryloxazolidin-2-one-3-ylacetic acid ester. The haloacetic acid ester is represented by the formula "X—CH$_2$COOalk in the foregoing reaction scheme, wherein "X" is chloro or bromo and "alk" is C$_1$ to C$_4$ alkyl. Preferably, the alk group is t-butyl or ethyl. Examples of haloacetic acid esters are t-butyl bromoacetate, ethyl bromoacetate, methyl chloroacetate, t-butyl chloroacetate, methyl bromoacetate, isopropyl bromoacetate, and like esters. Preferred halo esters are t-butyl bromoacetate and ethyl bromoacetate.

The deesterification of the oxazolidinone acetic acid ester is achieved by standard deesterification procedures. For example, the t-butyl ester group is removed upon treatment of the ester with trifluoroacetic acid while other lower alkyl esters such as the ethyl ester can be saponified.

The oxazolidinone acetic acid is converted to either the acid halide (5a, X'=halogen, and preferably trifluoroacetic acid (X'=OCOCF$_3$), or with a phosphoryl halide (X'=—O—P(=O)X$_2$)). The acid halide, and preferably the chloride, is a preferred source of the ketene for use in the subsequent cycloaddition reaction. The acid chloride is obtained, for example, with oxalyl chloride in an inert solvent such as benzene, toluene, or xylene. Other conventional acid halide-forming reagents may also be used.

The (S)-4-aryloxazolidin-2-one-3-ylacetyl halide or anhydride is the functionalized form of the chiral auxiliary moiety used to form the β-lactam ring of the azetidinone intermediates represented by the above formula.

The acetyl halide (5a) is reacted with the imine (formed with a benzylamine and a 3-arylacrolein) to yield the 1-benzyl-3β-[(S)-4-aryloxazolidin-2-one-3-yl]-4β-(2-arylvinyl)azetidinone (formula 1, Y=—CH=CH—). A minor amount of isomeric cycloaddition product is also formed. The cycloaddition reaction is illustrated in the following reaction scheme:

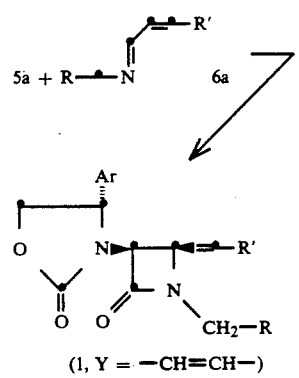

(1, Y = —CH=CH—)

wherein R, R' and Ar have the same meanings as defined above.

The reaction is carried out at a temperature between about −78° C. and about 25° C. in an inert organic solvent (such as methylene chloride, chloroform, toluene, or a di- or trichloroethane) in the presence of a tri-(C$_1$ to C$_4$ alkyl)amine. A solution of the imine (6a) is added to a solution of the acetyl halide 5a in an inert solvent containing the tri(C$_1$ to C$_4$ alkyl)amine in an amount in excess of the stoichiometric amount. The tri(C$_1$ to C$_4$ alkyl)amine is added to the solution of the acetyl halide 5a prior to addition of the imine 6a. The acid derivative 5a and the imine are mixed at a temperature between about −80° C. and about −50° C. form in situ the ketene. The imine 6a is then added to form the azetidinone. Conveniently, the solvent for the imine is the solvent in which it was prepared as described below. Such solvents as benzene, toluene, and the xylenes are suitable. Following the addition of the imine, the reaction is warmed and maintained at about 0° C. for from 2 to 4 hours. The mixture of the major isomer and the minor isomer is recovered from the reaction mixture as follows. The reaction mixture is diluted with a water-immiscible organic solvent such as methylene chloride or chloroform and is first washed with a weak acid (such as tartaric acid or citric acid) then washed with saturated, aqueous alkali metal bicarbonate. After drying, the washed mixture is evaporated to dryness. Most often the major isomer can be crystallized from an ethyl acetate-hexanes solution (approximately 30% hexanes by volume) of the residue. Alternatively, the major isomer can be separated from the minor isomer by chromatography over a silica gel column that is eluted in a step-wise or a gradient method. Step-wise elution with an ethyl acetate/methylene chloride solution containing a percentage ethyl acetate by volume of from approximately 20% will generally elute the azetidinone while an eluant with increased polarity (approximately 40%-50% ethyl acetate by volume) will elute the minor component. After chromatography the azetidinone can be recrystallized to enhance its purity.

Condensing a 3-arylacrolein with benzylamine or a substituted benzylamine in a suitable solvent yields the imine 6a employed in the cycloaddition. In the cycloaddition a small excess over the stoichimetric amount of the acrolein is preferably used. The water produced during the condensation is removed either by using a drying agent or by azeotropic distillation. Drying agents such as magnesium sulfate or molecular sieves are suitable. The condensation reaction is carried out in organic solvents such as diethyl ether or an aromatic hydrocarbon such as benzene or toluene.

The condensation reaction proceeds rapidly at a temperature between about 25° C. and 65° C. either in the presence of a drying agent or during the azeotropic removal of water from the reaction mixture.

Examples of 3-arylacroleins which can be used to form the imine are represented by the formula

wherein R' is phenyl, $C_1$ to $C_4$ alkylphenyl, $C_1$ to $C_4$ alkoxyphenyl, halophenyl, furyl or naphthyl. Examples of such aldehydes are cinnamaldehyde, 4-methylcinnamaldehyde, 3-ethylcinnamaldehyde, 4-ethoxycinnamaldehyde, 3-methoxycinnamaldehyde, 3-t-butyloxycinnamaldehyde, 3-ethoxycinnamaldehyde, 3-bromocinnamaldehyde, 2-(2-furyl)acrolein, 2-(2-naphthyl)acrolein, and like aldehydes.

Examples of benzylamines useful in the imine formation are benzylamine and the $C_1$ to $C_4$ alkyl, $C_1$ to $C_4$ alkoxy, and the halo-substituted benzylamines such as 4-methylbenzylamine, 3-chlorobenzylamine, 3,4-dichlorobenzylamine, 4-methoxybenzylamine, 2-bromobenzylamine, 3-ethylbenzylamine, 3,4-dimethylbenzylamine, 2,4-dimethylbenzylamine, 4-chloro-3-methylbenzylamine, 4-isopropylbenzylamine, 4-(t-butyl)benzylamine, and the like.

The imine 6a can be employed in the cyclo-addition reaction without prior isolation. For example, the reaction mixture in which the imine is prepared may be used directly in the cycloaddition.

The azetidinone represented by the above formula wherein Y is a group of the formula —CH=CH— and R' is an m-alkoxyphenyl group is a valuable intermediate in a process for the preparation of 3-hydroxy-1-carba-1-dethiacephem-4-carboxylic acid esters. This process is further described in David A. Evans et al., U.S. Pat. No. 4,673,737, issued June 16, 1987, and in David A. Evans et al., Tetrahedron Letters, 26, pp. 3787-3790 (1985).

According to the process, the (S)-4-aryloxa-zolidin-2-one-3-ylacetyl halide (5a) is reacted in the cycloaddition reaction described above with the imine (6a), formed with a benzylamine and a m-alkoxycinnamaldehyde, to provide the azetidinone represented by the above formula wherein Y is a group of the formula —CH=CH— and R' is a m-($C_1$ to $C_4$ alkoxy)phenyl group. The azetidinone is hydrogenated to yield the corresponding 4β-[2-(m-alkoxyphenyl)ethyl] azetidinone, and the latter is reacted with lithium-ammonia in the presence of t-butyl alcohol to reduce the phenyl ring, and remove the chiral auxiliary and the 1-benzyl group to provide a 3β-amino-4β-(2-(5-alkoxycyclohex-1,4-dienyl)ethyl]azetidinone. The 3-amino group of the azetidinone is protected with a conventional amino-protecting group and the 3β-protected-aminoazetidinone is subjected to ozonolysis to yield the β-keto ester $C_1$-$C_4$ alkyl 5-[3β-(protected amino)azetidin-2-one-4β-yl]—3-oxopentanoate.

The β-keto ester ozonolysis product is converted to the o-diazo derivative and the diazo derivative is cyclized with a rhodium (II) carboxylate complex to provide the 3-hydroxy-1-carba-1-dethiacephalosporin ester.

The above process for converting the azetidinone to a 3-hydroxy-1-carba-1-dethiacephalosporin is illustrated in the following reaction Scheme II.

Scheme II

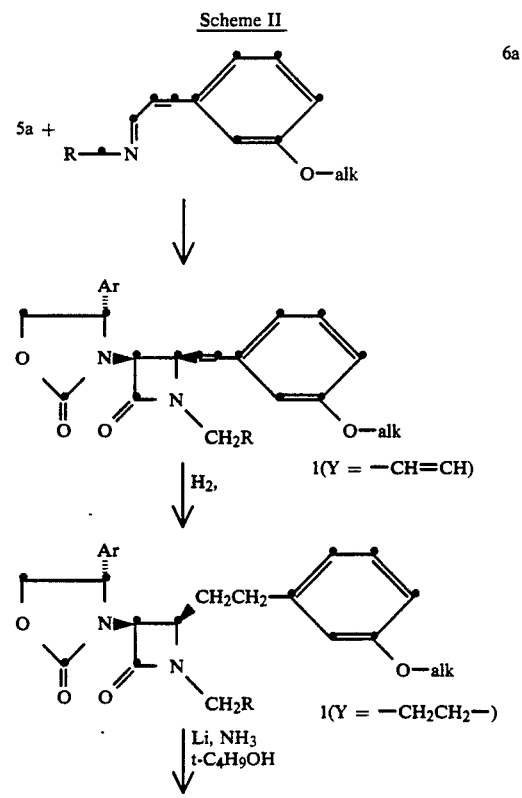

-continued
Scheme II

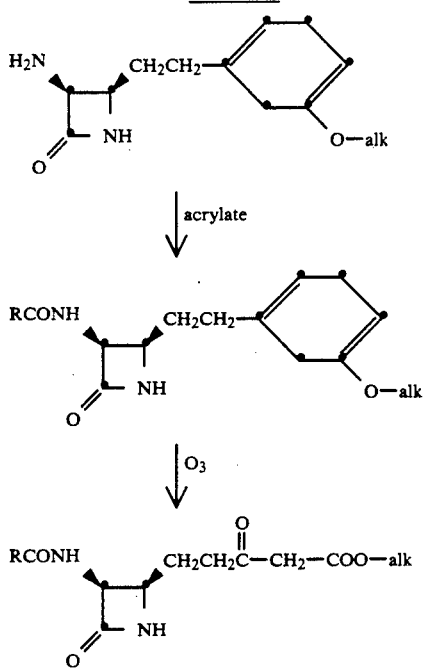

More specifically, as represented in the above Scheme, the azetidinone (Y=—CH=CH—) is hydrogenated over a palladium catalyst such as a supported palladium catalyst (for example, 5% or 10% palladium on carbon, barium carbonate, or other suitable support). The reduction can be carried out at atmospheric pressure, or at somewhat elevated pressures, in an inert solvent at room temperature. Suitable inert solvents for the hydrogenation include methylene chloride, di- or trichloroethane, tetrahydrofuran, methyl alcohol, ethyl alcohol, or ethyl acetate. The product of the hydrogenation, 4$\beta$-[2-(m-alkoxyphenyl)ethyl]azetidinone, is isolated by conventional procedures.

The 4$\beta$-[2-(m-alkoxyphenyl)ethyl]azetidinone is reduced to the 3$\beta$-amino-4$\beta$-[2-(5-alkoxycyclohex-1,4-dienyl)ethyl]azetidin-2-one (7a) with lithium in liquid ammonia containing t-butyl alcohol. The reduction is carried out by dissolving lithium in liquid ammonia and cooling the solution to between about $-50°$ C. and about $-90°$ C. An excess of t-butyl alcohol is added followed by the addition of a solution of the azetidinone in an inert solvent. The solution of the azetidinone may contain t-butyl alcohol as a cosolvent. Suitable solvents for the azetidinone include tetrahydrofuran, dimethoxyethane, or like solvent. The reduction is carried out at a temperature between about $-30°$ C. and about $-90°$ C. and preferably at between about $-70°$ C. and about $-80°$ C.

After the solution of the azetidinone is added, the reduction mixture is stirred for about 30 minutes to about 2 hours. Small, laboratory-size reductions are usually stirred in the cold for about 30 minutes, while larger, manufacturing-scale reductions require somewhat longer reaction times for complete reduction to the diene 7a.

The reduction of the m-(alkoxyphenyl group) also removes the chiral auxiliary moiety, incorporated via the cycloaddition with 6a, leaving the 3-amino group. The reduction also removes 1-benzyl or 1-substituted benzyl group, leaving a primary azetidinone amide group.

The next step in the reaction scheme is the protection of the free amino group of the 3-aminoazetidinone 7a. The amino group can be protected after first isolating the 3-amino-azetidinone or protected directly in the reaction mixture after the lithium-in-ammonia reduction of the preceding step is quenched. Specifically, following the reduction the reaction mixture is treated with sufficient benzene to discharge the blue color of the mixture. Ammonium acetate is added to the mixture and the bulk of the ammonia is distilled off. The solvent and any remaining ammonia are evaporated. The residue 7a is treated with water and a water miscible organic solvent such as tetrahydrofuran and the mixture or solution is acidified to a pH between about 7 and about 9. The solution of 7a is then treated with an acylating agent to provide the 3$\beta$-acylamino-4$\beta$-[2-(5-alkoxycyclohex-1,4-dienyl)ethyl]azetidinone 8a. The 3$\beta$-amino group is acylated to protect its integrity during the subsequent ozonolysis step in the process.

The acylating agent may be formed with any carboxylic acid that possesses an acyl residue which is stable in the subsequent ozonolysis step of the process. The carboxylic acid can be, for example, an alkylcarboxylic acid such as acetic acid, propionic acid, butyric acid, and the like; an arylcarboxylic acid (such as benzoic acid or napthoic acid) which may be optionally substituted by lower alkyl, lower alkoxy, or halogen groups or an arylacetic acid such as phenylacetic acid, phenoxyacetic acid, phenylthioacetic acid, and such acids optionally substituted. The desired carboxylic acid is first converted to a more active acylating agent, such as an acid chloride, acid anhydride or an active ester formed with a haloformate group (such as a $C_1$ to $C_4$ alkyl chloroformate, and specifically ethyl chloroformate and iso-butyl chloroformate.)

The acylating agent also can be an aryloxy-carbonyl halide such as benzyloxycarbonyl chloride or p-nitrobenzyloxycarbonyl chloride.

Preferred acylating agents are represented by the formula

wherein R is $C_1$-$C_6$ alkyl; a phenyl group

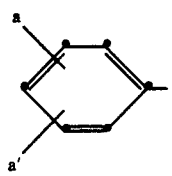

wherein a and a' independently are hydrogen, $C_1$-$C_4$ alkyl, $C_1$-$C_4$ alkoxy or halogen; a group represented by the formula

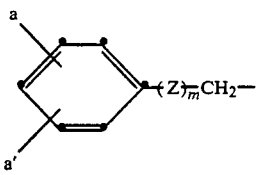

wherein Z is O or S, m is 0 or 1, and a and a' have the same meanings as defined above: or R is R°$_1$-O wherein R°$_1$represents C$_1$ to C$_4$ alkyl, C$_5$ to C$_7$ cycloalkyl, benzyl, nitrobenzyl, methoxybenzyl, or halobenzyl; and W is chloro, bromo, or an anhydride-forming group represented by the formula

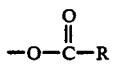

wherein R has the same meanings as defined above.

Examples of preferred acyl halide acylating agents represented by the above formula are acetyl chloride, acetyl bromide, butyryl chloride, propionyl chloride, benzoyl chloride, 4-chlorobenzoyl chloride, 4-methylbenzoyl chloride, phenoxyacetyl chloride, 4-chlorophenoxyacetyl chloride, phenylacetyl chloride, 3-ethylphenylacetyl bromide, phenylmercaptoacetyl chloride, 4-chlorophenylmercaptoacetyl chloride, benzyloxycarbonyl chloride, cyclohexyoxycarbonyl chloride, cyclopentyloxycarbonyl chloride, ethoxycarbonyl chloride, and the like.

Examples of preferred anhydride acylating agents represented by the above formula are benzoic acid anhydride, phenoxyacetic acid anhydride, phenylacetic acid anhydride, p-chlorophenoxyacetic acid anhydride, phenylmercaptoacetic acid anhydride, di-t-butyl dicarbonate, dibenzyl dicarbonate, di-(p-nitrobenzyl) dicarbonate, di-ethyl dicarbonate, di-cyclohexyl dicarbonate, and like anhydrides.

The N-acylated reduction product 8a is recovered from the mixture by extraction and is purified by chromatography over silica.

The 3-acylaminoazetidinone 8a is then converted to the β-keto ester 9a by ozonolysis. The ozonolysis is preferably carried out in 50% methyl alcohol in dichloromethane or other suitable solvent mixture, at a temperature between about −5° C. and about −80° C. The ozone is passed into the solution of the diene 8a until the reaction is complete. The ozone is most conveniently added to the reaction mixture from a conventional ozone generator in a stream of air. The completion of the ozonolysis may be determined by the use of a diene indicator such as solvent red (Sudan III, Aldrich Chemical Company). Following completion, any ozonide and excess ozone in the mixture is destroyed in the cold with dimethyl sulfide or other suitable reducing agent such as a sulfite or phosphite. The product 9a is then recovered from the mixture by conventional techniques. For example, the reaction mixture is allowed to warm to room temperature and then poured into brine. The product is extracted with a water-immiscible solvent such as methylene chloride. The β-keto ester 9a may be further purified by chromatography over silica.

As represented in the following scheme, the β-keto ester 9a is then converted to the 7-acylamino-1-carba(1-dethia)-3-hydroxy-3-cephem ester 11a via diazo compound 10a. The cyclization of the diazo ester to the 1-carbacephalosporin is catalyzed with a dirhodium (II) tetracarboxylate complex.

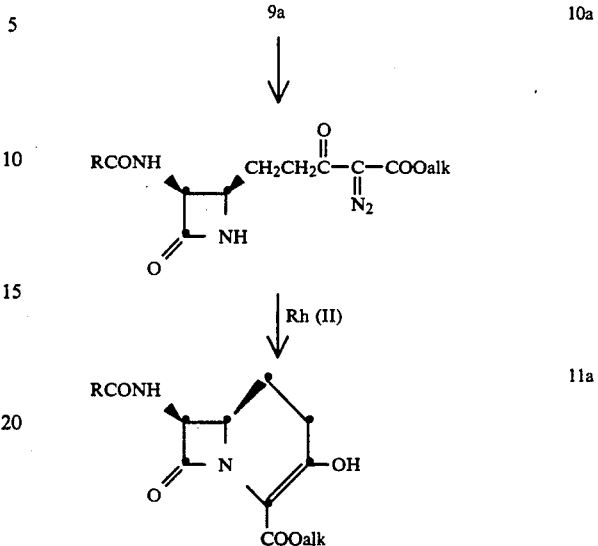

The β-keto ester 9a is best converted to the diazo ester 10a in an inert solvent such as acetonitrile, dichloromethane, trichloroethane, or the like, with p-toluenesulfonyl azide (tosyl azide) in the presence of a hindered tertiary amine (such as di(isopropyl)ethylamine). The reaction is conveniently carried at room temperature. Generally, the tosyl azide is used in an excess of the stoichiometric amount while the amine is used in an amount of about one-fourth of the stoichiometric amount. The diazo ester is recovered from the reaction mixture by partitioning the mixture between a water immiscible solvent (such as methylene chloride) and brine containing some tartaric acid or citric acid. The diazo ester obtained from the extract is purified via chromatography over silica then recrystallized.

As shown in the above reaction scheme, the ester moiety "alk" of 10a becomes the ester group of the 1-carba-1-dethiacephalosporin 11a upon cyclization. Ester groups such as the lower n-alkyl groups, (in particular the methyl and ethyl groups), are less readily removed form the carboxy function than other groups. From a synthetic point of view, it may be desirable to form a 1-carba-1-dethiacephalosporin 11a wherein the ester group is a conventional carboxy-protecting group that is more readily removed than methyl or ethyl. A one-carba-one-dethiacephalosporin with a conventional carboxy-protecting group (i.e., other than those defined for the variable alk) can be obtained from the transesterification of the ester group (alk) of 10a to diazo ester 10b as shown below.

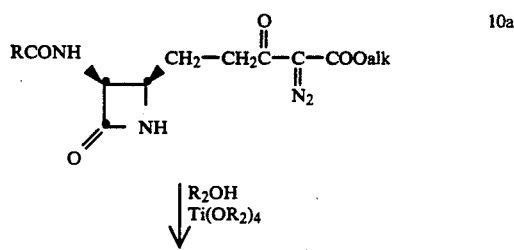

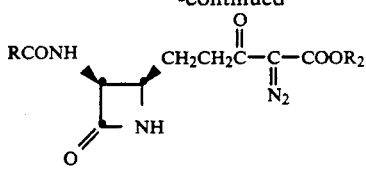

10b

In the above formulas, the variables R and alk have the previously defined meanings and $R_2$ is allyl, 2,2,2-trichloroethyl, 2,2,2-tribromoethyl, β-tri($C_1$ to $C_4$ alkyl)-silylethyl, benzyl, $C_1$ to $C_4$ alkylbenzyl, $C_1$ to $C_4$ alkoxybenzyl, nitrobenzyl, or chlorobenzyl. out by mixing an excess of the alcohol, $R_2OH$, with titanium tetraisopropoxide and removing isopropyl alcohol by evaporation. The diazo ester, 10a, is added to a solution of the $Ti(OR_2)_4$ in excess alcohol, and in an inert solvent if necessary, and the solution is maintained at a temperature between about 25° C. and about 45° C. until transesterification is complete.

Inert solvents for the transesterification reaction include for example, methylene chloride, di- or trichlorethane, chloroform, acetonitrile, tetrahydrofuran, or dioxane. When benzyl alcohol is used in the transesterification to form the $R_2$ester group, it also may serve as a solvent for the process.

The diazo ester 10a or the diazo ester 10b obtained via the transesterification process is then cyclized to 1-carba-1-dethiacephalosporin 11a with dirhodium (II) tetraacetate in chloroform at the reflux temperature. The reaction is heated for about 15 minutes to about one hour and the 7-acylamino-3-hydroxy-1-carba(1-dethia)-3-cephem-4-carbbxylic acid ester is recovered as such from the reaction mixture or is first converted to a corresponding derivative which is then isolated.

The 3-hydroxy 1-carba-1-dethiacephalosporin ester may be recovered from the reaction mixture by first diluting the mixture with water or brine, acidifying the mixture, and then extracting the mixture with a solvent such as ethyl acetate or methylene chloride. The extract is washed, dried and evaporated to provide the product. The product may be further purified by chromatography and recrystallization.

In a preferred synthesis of 3-hydroxy-1-carba-1-dethiacephalosporins, using the reactions outlined above, L-phenylglycine (1a, Ar=phenyl) is converted to the ethylcarbamate with ethyl chloroformate, the carbamate acid is reduced with borane-dimethyl sulfide to L-1-ethoxycarbonylamino-1-phenylethanol (3a, alk=ethyl), and the phenylethanol is cyclized with n-butyllithium to (S)-4-phenyloxazolidin-2-one (4a). The latter is converted to 5a via alkylation with ethyl bromoacetate, saponification, and treatment of the acid with oxalyl chloride.

The (S)-4-phenyloxazolidin-2-one-3-ylacetyl (5a) chloride is condensed with the imine formed with benzylamine and m-methoxycinnamaldehyde (formula 6a, alk=methyl, R=phenyl) to form the azetidinone 1, (wherein Ar=phenyl, alk=methyl). Catalytic reduction of 1 over 5% Pd-C provides azetidinone, (wherein $Y=CH_2-CH_2-$) which on reduction with lithium in liquid ammonia and t-butyl alcohol yields the 3-aminoazetidinone (7a, alk=methyl). Without isolation, the 3-aminoazetidinone is acylated with di-(t-butyl) dicarbonate to form the 3-(t-butyloxycarbonylamino)azetidinone (8a, $R_1$=t-butyloxy, alk=methyl). Ozonolysis of the 3-(t-BOC) amino-protected diene product in 50% methyl alcohol in dichloromethane provides the β-keto methyl ester 9a. The β-keto methyl ester is reacted in acetonitrile with tosyl azide in the presence of di(isopropyl)ethylamine to provide the diazo methyl ester (10a, $R_1$=t-butyloxy, alk=methyl). The transesterification of the diazo methyl ester to the corresponding benzyl ester is carried out in excess benzyl alcohol with titanium tetra(isopropoxide) with heating at about 36° C. for 42 hours. The diazo benzyl ester is treated in refluxing chloroform with dirhodium (II) tetraacetate to provide benzyl 7β-(t-butyloxycarbonylamino)-3-hydroxy-1-carba-(1-dethia)-3-cephem-4-carboxylate.

A second method for making a 3-hydroxy 1-carba-1-dethiacephalosporin is set forth in M. Hatanaka et al., Tet. Letters, 24, pp. 4837–4838 (1983). The method of Hatanaka et al. is similar to that of Evans in that the β-lactam ring is first formed from a 2+2 cyclo-addition. However, Hatanaka et al. form the 6-membered ring from an acetate ester fragment appended to the 1-position nitrogen which serves as a nucleophile in the Dieckmann condensation step.

In the following Preparations and Examples, the terms dimethylformamide, nuclear magnetic resonance spectra, are abbreviated DMF and n.m.r., respectively.

In conjunction with the n.m.r. spectra, the following abbreviations are used: "s" is singlet, "d" is doublet, "dd" is doublet of doublets, "t" is triplet, "q" is quartet, and "m" is multiplet, respectively.

The n.m.r. spectra were obtained on a General Electric QE-300 300 MHz instrument. The chemical shifts are expressed in δ values (parts per million downfield from tetramethylsilane).

Experimental Section

EXAMPLE 1

LY213735 Bis(DMF) solvate

A. Acylation

DMF (81.2 ml) was cooled to −20° C. then sodium 2-(R)-2-(p-hydroxyphenyl)-2-(((Z)-methyl but-2-en-2-yloate)amino)acetate (5.70 g, 19.84 mmol) was added to give a white suspension. The suspension was cooled to −45° C. (The pH of the solution was approximately 7.5). Methanesulfonic acid (17.1%, 3.08 mmol, 0.2 ml) was added to the suspension followed immediately by the addition of dimethylbenzylamine (2%, 0.054 ml, 0.37 mmol) and methyl chloroformate (1.42 ml, 18.4 mmol), all the while maintaining the temperature of the suspension below −45° C. The suspension was stirred for an additional 50 minutes at a temperature that fluctuated between −50° and −45° C. p-Nitrobenzyl 7-(R)-7-amino-3-chloro-3-(1-carbadethiacephem)-4-carboxylate (6.33 g, 18.4 mmol, dissovled in DMF (20 ml)) was added to the suspension while maintaining the temperature of the suspension below −45° C. The suspension was stirred for an additional 1.5 hours then warmed over a 10 minute period to 0° C. give the acylated product.

B. Deprotection

To the solution from A ("Acylation") above, water (6.48 ml), concentrated hydrochloric acid (11.6 ml), and zinc dust (3.34 g, 51.05 mmol, 2.83 equivalents) were added while maintaining the mixture from between 0 to 10° C. The reaction mixture was stirred at room temperature for approximately 5 hours yielding a solution with a red-orange color and a pH of 3.8. Additional concentrated hydrochloric acid (8.9 ml) was introduced and the reaction mixture was stirred for an additional 15 minutes at approximately 20° C. The reaction mixture was cooled to 15° C. and the pH of the mixture was raised from 0.99 to 2.9 by the addition of triethylamine (approximately 14 ml). The mixture was stirred for 15 mintues then filtered through Whatman papers and glass filters which were washed with DMF (10 ml). The filtrate was placed in a clean flask, cooled to 15° C., and the pH of the solution was taken to 4.6 by the addition of triethylamine. The solution was seeded with crystals of LY213735. The seeded solution was stirred for 30 minutes then the pH was taken to 5.6 by the addition of triethylamine. The developing mixture was stirred for 35 minutes then filtered. The collected solid was dried in vacuo at room temperature for 3 days to give LY213735 bis(DMF) solvate. (2.99 g, 32.4% yield).

The dried LY213735 bis(DMF) was suspended in 9:1 DMF:water (30 ml) and the pH of the suspension was taken to 1.1 by the addition of concentrated hydrochloric acid. The suspension was stirred for approximately 10 minutes until a solution formed. The pH of the solution was slowly raised to 5.6 by the addition of triethylamine while maintaining the temperature of the solution at 5° C. Upon reaching pH 5.6 the mixture was stirred for 30 minutes and filtered. The collected solid was dried in vacuum at room temperature for 24 hours to give crystalline LY213735 bis(DMF) solvate. n.m.r.: (300 MHz, $D_2O/DCl$) δ: 8.1 (s, 7H) (excess of DMF); 7.6 (2H, d); 7.1 (2H, d); 6.5 (1H, d); 6.3 (1H, s); 4.0 (1H, m); 3.1 (25H(DMF), s); 2.9 (27H(DMF), s); 2.6 (2H, m).

EXAMPLE 2

LY213735 mono(DMF) solvate

A. Acylation

Under a nitrogen atmosphere, sodium 2-(R)-2-(p-hydroxyphenyl)-2-(((Z)-methyl but-2-en-2-yloate)amino)-acetate (40.57 g, 141.2 mmol) was suspended in DMF (578 ml) that had been cooled to −20° C. The suspension was further cooled to −45° C. and methanesulfonic acid (0.33 ml, 5.14 mmol), dimethylbenzyl amine (0.41 ml, 2.69 mmol), and methyl chloroformate (10.62 ml, 137.4 mmol) were added with a syringe. During the addition the temperature of the DMF solution was maintained in a range between −45° to −50° C. The resultant suspension was stirred for an additional 15 minutes at −50° C. p-Nitrobenzyl 7-(R)-7-amino-3-chloro-3-(1-carbadethiacephem)-4-carboxylate (128.4 mmol in DMF (in 190 ml)) was added over a 50 minute period, and the resultant reaction mixture was then stirred at −45° C. for 2 hours. The reaction mixture was warmed to −10° C. over a 20 minute period to give a solution of the acylated, carboxy-protected product.

B. Deprotection and Crystallization

To the solution from paragraph A above, water (48.8 ml), concentrated hydrochloric acid (87.3 ml), and zinc dust (25.18 g, 385.2 mmol) were added over a 15 minute period while maintaining the temperature of the reaction mixture between 0° to about 10° C. A final portion of concentration hydrochloric acid (63.3 ml) was added to the solution and the solution was stirred at room temperature for 4.75 hours. The solution was cooled to 15° C., the pH was adjusted to 2.9 by the addition of triethylamine (approximately 100 ml), and the mixture was stirred for an additional 15 minutes. The mixture was filtered to recover the zinc residue then the filtrate was cooled to 15° C. and the pH of the filtrate was raised to 4.6 by the addition of triethylamine. The mixture was seeded with the non-solvated form of LY213735 and stirred for 15 minutes. The growing suspension was slowly treated with triethylamine (1 drop every 3 seconds) to obtain a pH of 5.65. The resultant suspension was stirred for several minutes. Additional triethylamine was added to raise the pH of the suspension to 5.866. The resultant thick suspension was stirred for 20 minutes during which time the pH stabilized at 5.833. The suspension was filtered through No. 1 Whatman Paper, and the collected solid was dried in vacuo overnight at room temperature to give a wet mass of 46.49 g.

The wet cake was suspended in 9:1 DMF:water (425 ml) and the pH of the suspension was adjusted to 1.1 with concentrated hydrochloric acid (14 ml), resulting in a solution. After the solution had formed and the pH of the solution had stabilized, the solution was filtered through No. 1 Whatman Paper. The filtrate was cooled to 5° C. and the pH was raised to 5.2 with the addition of triethylamine. The mixture was stirred for approximately 30 minutes starting from a time when a suspension first started to form. During those thirty minutes the pH of the mixture dropped to 4.4 and then was taken back to 5.7 with triethylamine (a total of 22 ml). The suspension was stirred until the pH was relatively stable then filtered. The collected solid was washed with a 9:1 DMF:water (20 ml). The washed solid was dried in vacuo at room temperature under a nitrogen flow overnight to yield a mass of 1.83 g, 27.9% of the crystalline LY213735 mono(DMF) solvate.

n.m.r.: (300 MHz, $D_2O/DCl$) δ: 7.94 (1H, s, (DMF)); 7.24 (2H, d); 6.94 (2H, d); 5.14 (2H, d); 3.94 (1H, m); 2.97 (3H, s(DMF)); 2.89 (3H, s(DMF)); 2.50 (2H, m); and 2.61 (1H, m).

EXAMPLE 3

LY213735 Monohydrate from the Bis(DMF) Solvate

Water (16.4 ml), and a solution of tetrasodium ethylenediaminetetraacetate (EDTA) (0.03 g) in concentrated hydrochloric acid (0.8 ml) were combined and then LY213735 bis(DMF) solvate (3.0 g) was added. The resultant suspension was stirred until a solution was effected. Charcoal (Darco ®, 0.03 g) was added and the suspension was stirred for 10 minutes at 15° C. and then filtered through a HYFLO ® filter aid pad. The filter cake was washed with water (3 ml). The filtrate (plus the wash) was cooled to 10° C. The pH of the cooled filtrate was taken to 3.6 by the addition of triethylamine to give a thick white suspension. The suspension was stirred for 2 hours and filtered. The filter cake was washed with cold water then dried in vacuo at room temperature overnight to give 1.05 g of crystalline LY213735 monohydrate: Karl Fischer: 3.13% water; n.m.r.: (300 MHz, $D_2O/DCl$) δ: 7.03 (2H, d); 6.6 (2H, d); 5.0 (1H, d); 4.95 (1H, s); 3.6 (1H, m); 2.1 (2H, m); 1.0 (2H, m); 0.94 (1H, t); (x-ray: (The powder X-ray diffraction parameters and pattern are given above as Table 1).

Analysis Calculated for $C_{16}H_{18}N_3O_6Cl$: Theory: C, 50.07; H, 4.73; N, 10.95; Found: C, 50.20; H, 5.02; N, 11.17.

EXAMPLE 4

LY213735 Mono(DMF) Solvate from the Corresponding Bis(DMF) Solvate

A mixture of the mono(N',N-dimethylformamide) solvate and bis(N,N'-dimethylformamide) solvate compounds (a total of 70.64 g) was combined in the minimum amount of DMF (250 ml). The suspension was cooled to between 10° and 15° C. The pH of the cooled suspension was adjusted to 1.1 by the addition of concentrated hydrochloric acid. The acidified suspension was stirred until a solution was obtained. The pH of the solution was slowly adjusted to 5.8 with triethylamine, all the while stirring the solution very slowly (approximately 1 revolution per second). The resultant suspension was stirred slowly for 15 minutes while the pH was maintained between 5.7 and 5.8 then filtered. The filter cake washed with ethyl acetate and dried in vacuo overnight to yield 47.3 g of crystalline LY213735 mono(DMF) solvate. Karl Fischer: 8.72% water; n.m.r.:(300 MHz, $D_2O$/DCl) $\delta$: 7.9 ($\frac{1}{2}$H, s(DMF)); 7.4 (2H, d); 6.75 (2H, d); 5.45 (1H, d); 4.6 (1H, s); 3.75 (1H, m); 2.75 (2H, s(DMF)); 2.4 (2H, s(DMF)); 2.55 (2H, m); 1.45 (2H, m); X-ray: (The powder diffraction X-ray parameters and pattern for this compound are given above in conjunction with Table 2).

EXAMPLE 5

LY2I3735 Monohydrate from the Corresponding Mono(DMF) Solvate

Deionized water (300 ml), tetrasodium ethylenediaminetetraacetate (EDTA) (0.52 g, 1.2 mmol), and concentrated hydrochloric acid (14.2 ml) were combined and stirred first at room temperature then cooled to 15° C. LY213735 mono(DMF) solvate (47.0 g, 0.107 mole) was added to the solution and the resultant suspension became a solution after approximate 10 mintues of stirring. Charcoal (Darco ®, 0.5 g) was added and then the suspension was stirred for 10 minutes at a temperature between about 15° to 20° C. The suspension was filtered through an 0.5 inch pad of HYFLO ® filter aid. The filter cake washed with water (approximately 60 ml). The (combined) filtrate (and wash) was cooled to 15° C. and the pH was raised slowly (0.1 units per 5 minutes) to 1.7 by the addition of triethylamine. The cloudy solution was stirred for approximately 10 minutes to give a thick white suspension. The suspension was stirred for another 45 mintues. The pH of the suspension was then slowly raised to 3.5 by the addition of triethylamine. The pH of the suspension continued to rise spontaneously to 5.8 where upon several drops of concentrated hydrochloric acid were added to steady the pH at 5.75. The suspension was stirred for 1.5 hours at this pH 5.75 while maintaining the temperature of the suspension from between about 13 to about 16° C., then filtered. The filter cake was washed with water (60 ml) and was dried in vacuo at room temperature for overnight to give 36.06 g of a white solid.

The filtrate from the final filtration of the above paragraph was diluted with acetonitrile (400 ml), and chilled overnight to yield a white suspension. The suspension was filtered and dried in vacuo overnight to yield 2.48 g of a white solid.

The two lots of while solids (from the first and second paragraphs above) were combined in water (200 ml). The resultant suspension was stirred at approximately 10° C. for 1 hour and was filtered. The filter cake was washed with water (approximately 50 ml) was dried in vacuo overnight at room temperature to yield 28.39 g of crystalline LY213735 monohydrate: Karl Fischer analysis: 2.6% water; n.m.r.: (300 MHz, $D_2O$/Dcl) $\delta$:7.20 (2H, d); 6.75 (2H, d); 5.1 (1H, d); 5.0 (1H, s); 3.7 (1H, m); 2.7 ($\frac{1}{2}$H, s); 2.35 (2H, m); 1.05 (2H, m).

EXAMPLE 6

Hard gelatin capsules are prepared using the following ingredients:

|  | Quantity (mg/capsule) |
| --- | --- |
| LY213735 monohydrate | 200 |
| Starch flowable powder | 200 |
| Starch Flowable pattern with silicone 5% | 50 |
| Magnesium stearate | 2.5 |

The above ingredients are mixed and filled into hard gelatin capsules in 452.5 mg quantities.

EXAMPLE 7

A tablet formula is prepared using the ingredients below:

|  | Quantity (mg/tablet) |
| --- | --- |
| LY213735 monohydrate | 200 |
| Cellulose, microcrystalline | 200 |
| Silicon dioxide, fumed | 10 |
| Stearic acid | 5 |

The components are blended and compressed to form tablets each weighting 415 mg.

EXAMPLE 8

Suppositories each containing 200 mg of active ingredient are made as follows:

| LY213735 monohydrate | 200 mg |
| --- | --- |
| Saturated fatty acid glycerides to | 2000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 9

| Ready To-Use Aqueous Suspension | 200 mg/5 ml |
| --- | --- |
| LY213735 monohydrate | 210 mg |
| Cellulose with sodium carboxymethylcellulose | 95 mg |
| sucrose | 1.85 g |
| parafens | 3 mg |
| emulsion silicone | 2.5 mg |
| pluronic | 5 mg |
| flavor | 2 mg |
| color | 0.5 mg |
| purified water | q.s. to 5 ml |

The ingredients are sieved. The parafens are dissolved in hot purified water and, after cooling, the other ingredients are added. Sufficient purified water is added to produce the required volume. The suspension can then be passed through a colloid mill or homogenizer to produce a more elegant dispersion.

| Suspension for Reconstitution | |
|---|---|
| LY213735 monohydrate | 210 mg |
| Sucrose | 3 g |
| Xanthan gum | 5 mg |
| starch modified | 10 mg |
| emulsion silicone | 5 mg |
| sodium lauryl sulfate | 0.5 mg |
| methylcellulose | 2 mg |
| flavor | 0.5 mg |
| dye | |

The ingredients are seived and mixed in a suitable blender, such as a twin-shell, twin core Nauta ®-type, or ribbon blender. To constitute, a sufficient volume of purified water is added to produce the required volume.

I claim:

1. A crystalline mono(N,N'-dimethylformamide) solvate of the compound of the formula

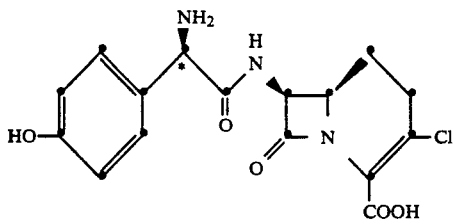

2. A compound of claim 1 which has the following X-ray powder diffraction pattern obtained with a nickel-filtered copper radiation of $\lambda = 1.5406$ Å wherein d represents the interplanar spacing and $I/I_1$ the relative intensity:

| d | $I/I_1$ |
|---|---|
| 13.18 | .12 |
| 10.90 | 1.00 |
| 7.69 | .11 |
| 6.80 | .07 |
| 6.02 | .20 |
| 5.37 | .07 |
| 5.12 | .10 |
| 4.90 | .07 |

| d | $I/I_1$ |
|---|---|
| 4.69 | .27 |
| 4.37 | .43 |
| 3.93 | .25 |
| 3.57 | .15 |
| 3.40 | .23 |
| 3.22 | .10 |
| 3.08 | .05 |
| 2.85 | .07 |
| 2.74 | .15 |

3. A crystalline bis(N,N'-dimethylformamide) solvate compound of the formula

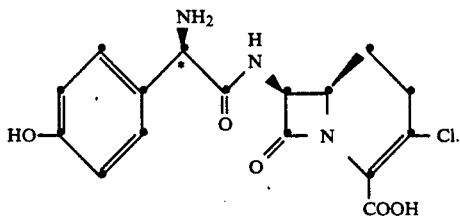

4. A compound of claim 3, which has the following X-ray powder diffraction pattern obtained with a nickel-filtered copper radiation of $\lambda = 1.5406$ Å wherein d represents the interplanar spacing and $I/I_1$ the relative intensity:

| d | $I/I_1$ |
|---|---|
| 20.10 | .03 |
| 12.44 | 1.00 |
| 10.27 | .07 |
| 8.58 | .08 |
| 6.91 | .03 |
| 6.60 | .05 |
| 6.23 | .08 |
| 5.43 | .13 |
| 4.74 | .09 |
| 4.41 | .09 |
| 4.19 | .40 |
| 3.62 | .05 |
| 3.52 | .05 |
| 3.39 | .03 |
| 3.34 | .03 |
| 3.14 | .10 |
| 3.02 | .07 |
| 2.86 | .06 |

* * * * *